United States Patent
Bry et al.

(10) Patent No.: US 9,335,236 B2
(45) Date of Patent: May 10, 2016

(54) DEVICE FOR SAMPLING DUST OR SOLID PARTICLES IN PARTICULAR FOR THE DETECTION OF EXPLOSIVES

(75) Inventors: Alain Bry, Le Veudois (FR); Alexandre Forzy, Tours (FR); Lionel Hairault, Blere (FR)

(73) Assignee: COMMISSARIAT A l'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 230 days.

(21) Appl. No.: 14/348,978

(22) PCT Filed: Oct. 4, 2011

(86) PCT No.: PCT/EP2011/067330
§ 371 (c)(1),
(2), (4) Date: Apr. 1, 2014

(87) PCT Pub. No.: WO2013/050066
PCT Pub. Date: Apr. 11, 2013

(65) Prior Publication Data
US 2014/0245843 A1  Sep. 4, 2014

(51) Int. Cl.
*G01N 1/02* (2006.01)
*G01N 1/24* (2006.01)
(Continued)

(52) U.S. Cl.
CPC ............... *G01N 1/24* (2013.01); *G01N 1/2211* (2013.01); *G01N 33/227* (2013.01); *G01N 2001/022* (2013.01); *G01N 2001/028* (2013.01)

(58) Field of Classification Search
CPC ................. G01N 2001/028; G01N 2001/022; G01N 1/24; G01N 1/22; G01N 1/2214; G01N 1/02; G01N 2001/2223; G01N 1/2273; G01N 1/2294; G01N 2001/2276; G01N 33/227; G01N 33/48714
See application file for complete search history.

(56) References Cited

U.S. PATENT DOCUMENTS

| 3,748,905 A | * | 7/1973 | Fletcher | ................ G01N 1/02 73/28.04 |
| 3,843,198 A |  | 10/1974 | Reynolds |  |
| 3,970,428 A | * | 7/1976 | Barringer | ............... G01V 9/007 422/83 |

(Continued)

FOREIGN PATENT DOCUMENTS

| DE | 102004002842 A1 | 8/2005 |
| EP | 0896213 A2 | 2/1999 |

(Continued)

OTHER PUBLICATIONS

International Search Report for PCT/EP2011/067330 dated Jun. 28, 2012.

(Continued)

*Primary Examiner* — David A Rogers
(74) *Attorney, Agent, or Firm* — Pearne & Gordon LLP

(57) ABSTRACT

It comprises a handle (1), an air flow amplifier (8) leading to a retention means (2) such as a cyclone via a passage (3), and a compressed air inlet device (7, 9) in the amplifier (8) that creates a strong suction of outside air, through the nozzle (4) capable of capturing even fine particles of low content up to a measurable quantity. Being completely devoid of electricity, this device is useful in hazardous atmospheres, in particular for detecting the presence of explosives after analysis of the particles collected by this device. It makes it possible to sample particles in extreme conditions of high or low temperatures.

13 Claims, 1 Drawing Sheet

Figure 1:
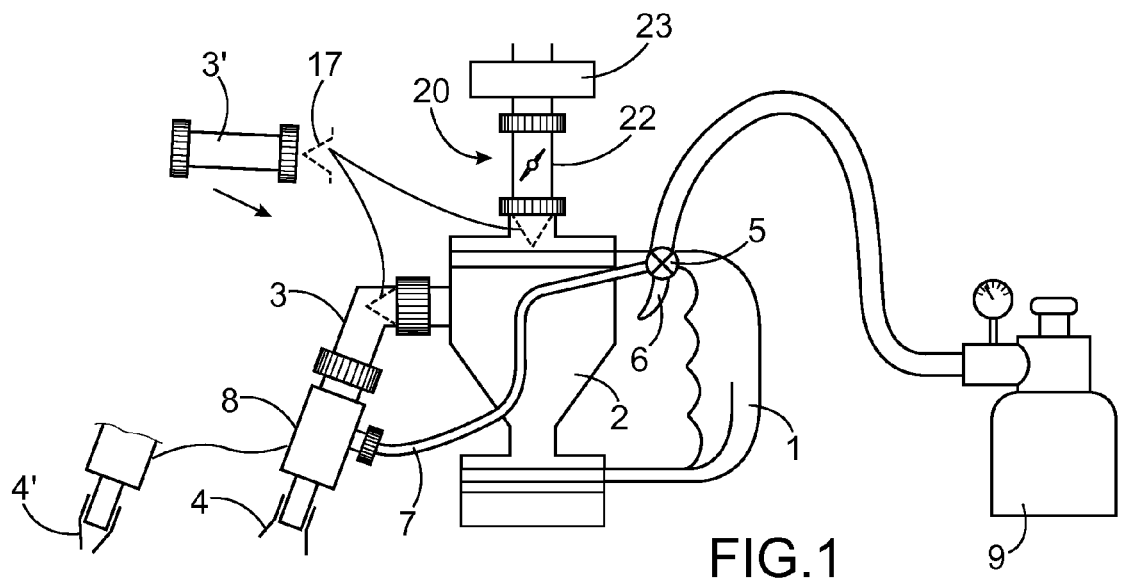

(51) Int. Cl.
*G01N 1/22* (2006.01)
*G01N 33/22* (2006.01)

(56) References Cited

U.S. PATENT DOCUMENTS

| | | | | | |
|---|---|---|---|---|---|
| 4,754,655 | A * | 7/1988 | Parker, III | ................ | G01N 1/08 73/863.23 |
| 4,909,090 | A * | 3/1990 | McGown | ............. | G01N 1/2214 73/863.12 |
| 5,663,561 | A * | 9/1997 | Franzen | ................ | H01J 49/145 250/282 |
| 5,751,897 | A * | 5/1998 | Van Alstyne | ............. | A62D 3/17 392/417 |
| 5,970,803 | A * | 10/1999 | Staples | ................ | G01N 1/2214 73/23.41 |
| 6,354,160 | B1 * | 3/2002 | Staples | ................ | G01N 1/2214 73/863.12 |
| 6,378,385 | B1 * | 4/2002 | Bowers | ................... | G01N 1/22 73/863.12 |
| 6,828,795 | B2 * | 12/2004 | Krasnobaev | ......... | G01N 27/622 324/464 |
| 6,861,646 | B2 * | 3/2005 | Motchkine | ............... | G01N 1/02 250/281 |
| 6,895,804 | B2 * | 5/2005 | Lovell | ................. | G01N 1/2202 73/31.05 |
| 6,978,657 | B1 * | 12/2005 | Baumann | ............ | G01N 1/2214 73/28.04 |
| 7,098,672 | B2 * | 8/2006 | Belyakov | ................ | G01N 1/22 324/451 |
| 7,833,802 | B2 * | 11/2010 | Henry | ...................... | G01N 1/24 250/282 |
| 7,997,119 | B2 * | 8/2011 | Wu | .......................... | G01N 1/14 324/239 |
| 8,113,069 | B2 * | 2/2012 | Settles | ................. | G01N 1/2226 73/863 |
| 8,307,723 | B2 * | 11/2012 | Novosselov | ......... | G01N 1/2202 73/864 |
| 8,353,223 | B2 * | 1/2013 | Bunker | ................. | B08B 7/0092 73/864.33 |
| 8,377,711 | B2 * | 2/2013 | Henry | ................... | G01N 21/658 356/36 |
| 8,561,486 | B2 * | 10/2013 | Novosselov | ........... | B01D 15/08 73/864.32 |
| 8,646,340 | B2 * | 2/2014 | Zhang | ..................... | G01N 1/24 73/863.11 |
| 2006/0115559 | A1 * | 6/2006 | Jones, Jr. | ............... | A22B 5/007 426/231 |
| 2006/0249671 | A1 * | 11/2006 | Karpetsky | ........... | G01N 27/624 250/288 |
| 2007/0068284 | A1 * | 3/2007 | Castro | ................... | G01N 1/2205 73/863.21 |
| 2007/0158447 | A1 * | 7/2007 | Bunker | ..................... | G01N 1/02 239/1 |
| 2008/0190218 | A1 * | 8/2008 | Riazanskaia | ............. | G01N 1/22 73/864 |
| 2009/0084201 | A1 * | 4/2009 | Almirall | ................ | G01N 1/405 73/864.81 |
| 2014/0130615 | A1 * | 5/2014 | Karki | ...................... | F23N 5/003 73/863.21 |

FOREIGN PATENT DOCUMENTS

FR 2965054 A1 3/2012
WO 0016064 A1 3/2000

OTHER PUBLICATIONS

Written Opinion for PCT/EP2011/067330.

* cited by examiner

DEVICE FOR SAMPLING DUST OR SOLID PARTICLES IN PARTICULAR FOR THE DETECTION OF EXPLOSIVES

The subject of the invention is a device for sampling dust or solid particles, which was designed for the purpose of detecting explosives, without excluding other applications, as the particles sampled can be of any nature compatible with the materials that constitute the device.

A conventional method for detecting the presence of certain substances, including explosives, consists in making use of specially-trained dogs. But despite the remarkable finesse of their sense of smell, the use of animals has the disadvantage of a low work capacity and a training period that is long and expensive. That is why other methods of detection have been developed. Certain are based on taking samples from the environment which are then analysed. The detection often concerns the vapour phase of the product that is sought to be recognised, with the sampling accomplished via suction devices; as the suction is in general at a low flow, these devices can more difficultly detect solid particles when their content in the atmosphere is low, all the more so that most of them can adhere to surrounding surfaces instead of being in suspension. But detecting vapours is not always possible: certain bodies, of which many explosives have a saturation vapour pressure that is very low, and therefore remain almost exclusively in solid state.

That is why it remains advantageous to sample, for the purposes of detecting them, samples of explosive materials in solid, dust or particle form. Common methods that do not make use of suction consist in performing a smear of the surface to be analysed in order to pull off particles and carry them off; but their use is prohibited in the frequent situations where one abstains from touching objects to be analysed in order to preserve them. Other methods make use of various forms of radiation in order to collect visual, spectroscopic or analytical information on explosives, but the latter have to be in substantial quantities and in massive form.

The device of the invention is based on the use of suction in order to sample solid particles. It can be distinguished from devices that accomplish the same function primarily under two aspects: it does not include any electrical actuation in order to make it possible to work even in hazardous atmospheres or in extreme temperatures (for example −40° to +60° C.), and it is designed in such a way as to suck a large flow even in the absence of an electric pump, in such a way as to allow for the sampling of particles in a substantial surrounding volume, which makes it possible to detect even very low content of them, while still creating a suction force that is sufficient to suck particles which may have become slightly stuck on surfaces in front of the device.

In a general form, the sampling device in accordance with the invention comprises a handle (1) for grasping established on a cyclone (2) for retaining sampled particles, a compressed air duct (7) responsible for the suction, and a mechanical valve (5) for closing the compressed air duct (7), controlled by an actuator (6), characterised in that it comprises an air amplifier (18), connected to the cyclone (2), via a passage (3), the compressed air duct (7) opens into the air amplifier (8) by being directed to the passage (3), and the air amplifier (8) comprises a circular slot (10) wherein the compressed air duct (7) opens, and a tapered groove (12) with a top directed towards the passage (3), extending the circular slot (9) and opening into a bore (13) of the amplifier (8), as such creating the amplification of the suction, and the amplifier is located between the cyclone and a nozzle (4) through which the particles enter into the device. The actuator can be a button, a trigger or a valve for example. As the valve is mechanical, it is entirely manual. The compressed air expanding in the nozzle produces a substantial driving of a flow of the outside air which can be from 100% to 1000% in comparable volumes of the compressed air in certain circumstances. This is what is called here the amplification of the suction and clearly distinguishes the invention from other devices wherein a more conventional but less effective suction is carried out. In comparison, U.S. Pat. No. 3,843,198 describes a device wherein a flow of compressed air contributes to sampling a sample of atmosphere, able to contain dust or particles, in front of a cutting tool, via a suction consecutive to a vacuum of the flow when it passes through a tightening: a suction duct extends from the location of sampling to the tightening by passing through a cyclone wherein the dust or particles are deposited. This suction via simple vacuum is however incapable of producing an amplification of the suction, i.e. a multiplication of the volume sampled in relation to volume of compressed air delivered, and even less so that the pressure losses through the suction duct, rather long and occupied by the cyclone, are substantial.

WO-A-00/16064 describes a device wherein the suction is consecutive to a blowing on an exterior circle, which makes it possible to detach the particles that are stuck on the sampling surface thanks to the pressure of the compressed air, but no amplification of the flow of compressed air is done to suck the sample since it is the compressed air itself which is sucked into the device.

U.S. Pat. No. 4,909,090 and WO-A-2009/139744 describe devices wherein the suction is carried out by a fan, i.e. an electrical device, contrary to what is desired here.

In the invention, the passage can in particular contain a filtering sieve with a large mesh in order to stop the large pieces sucked in. The particles sampled and recovered in the cyclone are then sent for analysis.

The valve and its actuator (trigger, etc.) are installed in the vicinity of the handle, and the compressed air duct can be oriented. This arrangement makes it possible to easily displace the nozzle in front of the locations where it is desired to take a sample without displacing the source of compressed air, which is generally a bottle left some distance away or carried by the operator in a knapsack or installed inside the hollow handle for small reservoirs if low autonomies are sufficient.

Figure 2:
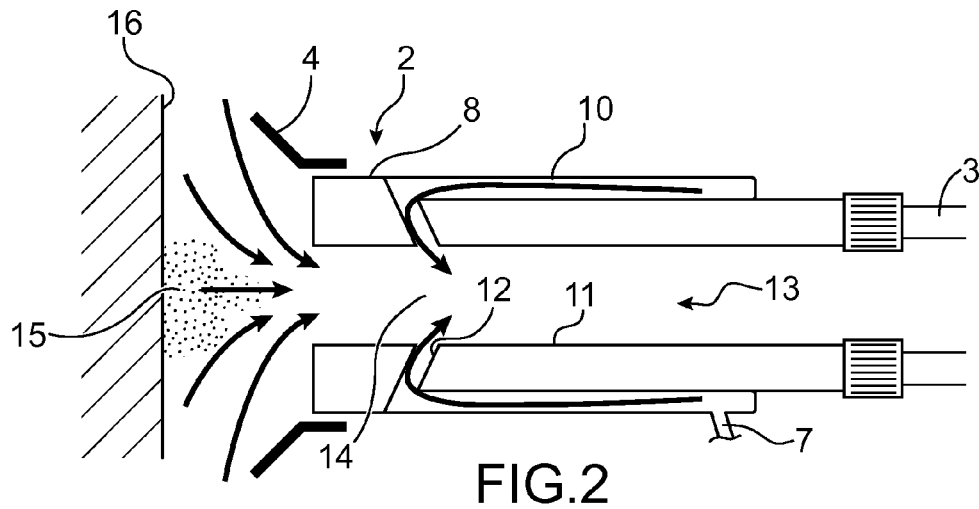
Figure 3:
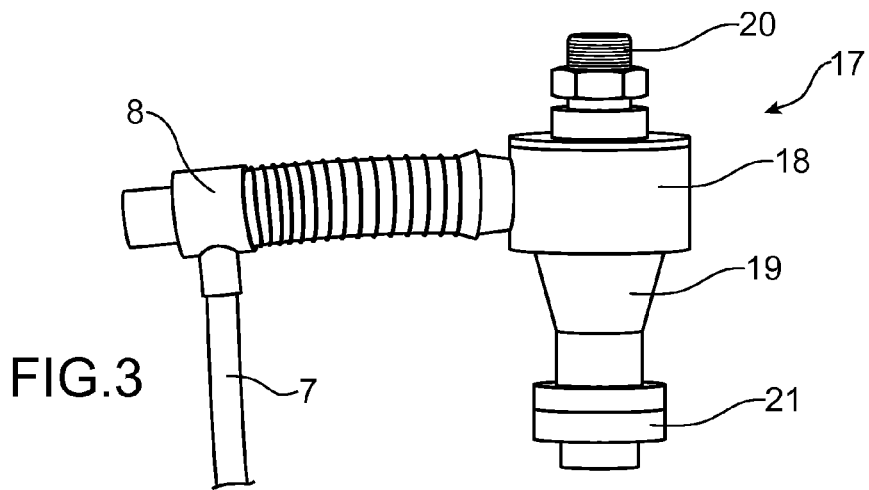

The invention shall now be described in more detail in liaison with the following figures:

FIG. 1 shows the invention as a whole;
FIG. 2 shows the suction nozzle and the amplifier;
and FIG. 3 shows an embodiment of the invention.

The embodiment described in FIG. 1 comprises a handle (1) grasped by the operator. The handle (1) is fixed on a cyclone (2) which is extended via a passage (3) of the cyclone (2) and an air amplifier (8), to which the passage (3) is connected by opposite ends; the passage (3) can also be oriented. The hose forming the passage (3) can be dismounted from the air amplifier (8) and from the cyclone (2). The connections are made by hose clamps, threadings, tightened adjustments or other means. The handle (1) further contains a manual valve (5) actuated by a button or a trigger (6); a flexible hose (7) is connected to the valve (5) positioned at a height from the handle (1) and is extended to the interior of the amplifier (8), in a manner that shall be described further on; its other end, after the manual valve (5), is connected to a bottle of compressed air (9) which extends some distance and can be positioned near the sampling location, carried by a vehicle, or by the operator himself in a knapsack. For small autonomies, the gas is contained in a bottle (9) that is disposable or that can be reused slid into the thickness of the handle (1). The manual valve (5) maintains the flexible cable (7) closed at rest, but when the trigger (6) is pressed, its valve is pushed back and allows for the ejection of compressed air in the nozzle (2). The end of the air amplifier (8) opposite the passage (3) carries a nozzle (4). An air outlet (20) in the upper portion of the cyclone (2) is overmounted by a valve (22) making it possible to close the air outlet (20) when the trigger (6) is pressed. This action forces the air to be blown by the nozzle (4) making it possible to better detach the particles before sucking them. Above the valve (22) is positioned a noise reducer (23). Filter sieves (17) or filters are established at the orifices of the cyclone (2), communicating with the passage (3) and with the valve (22) the air outlet (23). They are movable and have a large mesh. They stop the voluminous particles and are installed when the entry of impurities, which correspond to these particles, must be prevented; they can also be removed. The passage (3), here bent in order to direct the flow of air charged with particles towards the circular lateral wall of the cyclone (2) starting from a zone located at the foot of the cyclone (2), could be replaced with a different passage (3'), in particular straight, in order to create flows of air from a zone located at an altitude from the cyclone (2). Likewise, the nozzle (4), here flared toward this exterior zone from where the sampled air originates, in order to favour the suction, could be dismounted and replaced with another nozzle (4'), in particular narrowed toward said zone, in order to favour a blowing by the device. The passages (3, 3', etc.) and nozzles (4, 4', etc.) can belong to sets that accompany the device and are within reach of the operator. The fine particles stopped by the cyclone (2) fall into a lower reservoir (21). The lower reservoir (21) can be dismounted in order to be changed easily or recover the particles which are deposited therein.

Most of the parts of the device can be made of metal and are as such suitable for hot cleanings between two samplings; but certain parts can also be made from synthetic material (plastic) if it is acceptable to discard them and to replace them after a sampling.

FIG. 2 shall now be discussed. The air amplifier (8) is hollowed out with a circular slot (10) wherein the flexible cable (7) opens. The circular slot (10) opens onto the inner surface (11) of the nozzle (2) via a tapered groove (12), with a top directed towards the passage (3) and the cyclone (2). When the compressed air is given, it exits the circular slot (10) and the groove (11) and is directed on a slant through the bore (13) of the amplifier (8) then is corrected in order to flow tangentially to the inner surface (11) via a Coanda effect. This flow creates a vacuum at the centre of the bore (13) at the location (14), and the nozzle (4) is therefore effective in sucking the air of a large surrounding volume, with a force that is sufficient for detaching particles (15) that may be maintained on an adjacent wall (16), i.e. an amplification of the suction. The air and the particles driven then pass into the passage (3) and pass through the cyclone (2), wherein the particles are retained. As the cyclone (2) is downstream of the air amplifier (8) on the flow, it does not hinder the amplification.

An embodiment of the invention is described using FIG. 3. It comprises a cyclone (2'), with a peripheral body (18) for introducing gas, a cylindro-conical body (19) at the bottom of which the particles flow little by little while the gas exits through an upper opening corresponding to the air outlet (20), and the lower reservoir (21), in order to contain the particles. This construction allows for the sampling of finer particles, to a dimension of about one micron. The lower reservoir (21) can be dismounted in order to be changed or recover the particles that are deposited therein. The top of the peripheral body (18) can be dismounted for cleaning.

The tests have shown the effectiveness of the invention on the exterior of packaging containing explosives (Tolite or Hexomax). The sampling durations were less than one minute and the compressed air dispensed was a few hundred liters. The dust sampled shows the expected peaks in the chromatographic analyses.

Note that the hose of the passage (3) can be dismounted and replaced in order to change the direction of suction and as such improve accessibility to the particles.

The invention claimed is:

1. Device for sampling particles, comprising a handle (1) for grasping established on a cyclone (2) for retaining sampled particles, a compressed air duct (7) responsible for the suction, and a mechanical valve (5) for closing the compressed air duct (7), controlled by an actuator (6), characterised in that it comprises an air amplifier (18), connected to the cyclone (2), via a passage (3), the compressed air duct (7) opens into the air amplifier (8) by being directed towards the passage (3), and the air amplifier (8) comprises a circular slot (10) wherein the compressed air duct (7) opens, and a tapered groove (12) with a top directed towards the passage (3), extending the circular slot (9) and opening into a bore (13) of the amplifier (8), as such creating the amplification of the suction, and the amplifier is located between the cyclone and a nozzle (4) through which the particles enter into the device.

2. Device for sampling particles according to claim 1, characterised in that the means for retaining sampled particles comprises at least one cyclone (2).

3. Device for sampling particles according to claim 1, characterised in that the valve (5) and the actuator (6) are installed on the handle (1), and the compressed air duct (7) is flexible.

4. Device for sampling particles according claim 1, characterised in that the passage (3) is formed by a hose which can be oriented and which can be dismounted from the amplifier and from the means for sampling particles.

5. Device for sampling particles according to claim 4, characterised in that the passage (3) is provided with a movable filter (17) with a connection to the cyclone (2).

6. Device for sampling particles according to claim 1, characterised in that the cyclone (2) is provided with an air outlet (20) provided with a movable filter (17) and with a valve (22) capable of opening or closing the air outlet (20).

7. Device for sampling particles according to claim 6, characterised in that the air outlet (20) is provided with a device for reducing noise (23).

8. Device for sampling particles according to claim 1, characterised in that the nozzle (4) is movable from the air amplifier (8) and belongs to a set comprising a flared nozzle and a tapered nozzle in the direction of the particles to be sampled.

9. Device for sampling particles according claim 1, characterised in that the compressed air duct (7) exits into a bottle of gas (9).

10. Device for sampling particles according to claim 1, characterised in that the passage (3) is bent.

11. Device for sampling particles according to claim 1, characterised in that it comprises elements that can be discarded made from synthetic material.

12. Device for sampling particles according to claim 1, characterised in that it comprises a lower movable reservoir (21) that collects the sampled particles.

13. A process for sampling explosives, comprising the use of a device comprising a handle (1) for grasping established on a cyclone (2) for retaining sampled particles, a compressed air duct (7) responsible for the suction, and a mechanical valve (5) for closing the compressed air duct (7), controlled by an actuator (6), the device comprising an air amplifier (18), connected to the cyclone (2), via a passage (3), the compressed air duct (7) opens into the air amplifier (8) by being directed towards the passage (3), and the air amplifier (8) comprises a circular slot (10) wherein the compressed air duct (7) opens, and a tapered groove (12) with a top directed towards the passage (3), extending the circular slot (9) and opening into a bore (13) of the amplifier (8), as such creating the amplification of the suction, and the amplifier is located between the cyclone and a nozzle (4) through which the particles enter into the device.

\* \* \* \* \*